United States Patent [19]
Poulsen

[11] B 3,982,206
[45] Sept. 21, 1976

[54] SYSTEM FOR PROTECTION FROM LASER RADIATION

[75] Inventor: Peter D. Poulsen, Huntsville, Ala.

[73] Assignee: General Dynamics Corporation, San Diego, Calif.

[22] Filed: Nov. 27, 1974

[21] Appl. No.: 527,669

[44] Published under the second Trial Voluntary Protest Program on January 13, 1976 as document No. B 527,669.

Related U.S. Application Data

[62] Division of Ser. No. 280,312, Aug. 14, 1972, Pat. No. 3,871,739.

[52] U.S. Cl. .................... 331/94.5 T; 350/160 R
[51] Int. Cl.² .......................................... H01S 3/02
[58] Field of Search ............... 350/160; 331/94.5

[56] References Cited
UNITED STATES PATENTS

| | | | |
|---|---|---|---|
| 3,301,624 | 1/1967 | Morriss, Jr. .................... | 350/160 R |
| 3,455,627 | 7/1969 | Letter .................... | 350/160 R |
| 3,734,592 | 5/1973 | Sztankay et al. .................... | 350/160 R |

*Primary Examiner*—William L. Sikes
*Attorney, Agent, or Firm*—John R. Duncan

[57] ABSTRACT

A protective window for use with high-energy infrared radiation sources, such as lasers, is described, together with a method for manufacturing the window. For visual applications, the window basically includes a sheet of light transmitting material such as glass or quartz, which has a partially-reflecting surface coating, such as gold, which primarily reflects infrared radiation while transmitting visible light. The reflectivity of the coating may be improved by an infrared laser scanning technique. Finally, one or both surfaces of the window are coated with a visible-light transmitting synthetic resin which, if rapidly heated to a suitable temperature, vaporizes without leaving any residue. This vaporization carries away any contamination, such as dirt or dust, on the resin coating, leaving a very clean reflection surface. In order to further protect the window, channels may be formed within the window through which a cooling fluid may be circulated to carry away any heat absorbed by the window when subjected to infrared irradiation. This window has a variety of uses, such as the protection of laboratory or factory workers using high-energy infrared radiation sources, defenses against laser weapons, in intermittent laser signaling devices, etc.

10 Claims, 2 Drawing Figures

SYSTEM FOR PROTECTION FROM LASER RADIATION

CROSS-REFERENCE TO RELATED APPLICATION

This application is a division of U.S. Pat. Application Ser. No. 280,312, filed August 14, 1972, now U.S. Pat. No. 3,871,739. The prior appleiation is assigned to General Dynamics Corporation.

BACKGROUND OF THE INVENTION

Recently, high-energy infrared lasers have been developed for a number of applications. Typically, $CO_2$ (10.6$\mu$m wavelength) lasers operating at irradiance levels to about one Kw/cm$^2$ and higher have been used in manufacturing plants as welding and drilling tools, for scoring semiconductor sheets, etc. Many high-power lasers are used in laboratories, both as investigatory tools and in research on laser systems. Devices using powerful lasers have also been developed for communications, range finding and other military and civilian purposes. Other high-energy infrared lasers using deuterium and hydrogen halidies are being developed.

The energy transmitted by these lasers can be very dangerous to personnel working with the lasers or others who accidentally intercept the beam. These beams can be very damaging to the eyes of such persons and, in the higher power ranges, can cause severe burns and other physical damage.

Simply interposing a filter which absorbs or diverts the laser beam has been found to be insufficient. The localized energy application is so great and so rapidly applied that the filter material is often immediately melted and/or vaporized. Even highly efficient reflectors may be destroyed when surface dirt or dust absorbs sufficient energy to cause localized overheating and destruction of the reflector, destroying its protective capacity.

Attempts to protect personnel against such laser beams without extreme measures have generally not been successful. One proposed system, as described in U.S. Pat. No. 3,578,842, utilizes an exploding mirror in an optical system which might be impinged by a laser system. The laser energy causes an explosive on the mirror to detonate, thereby protecting the operator while destroying the optical system. Preferably, of course, he should be protected while allowing his equipment to continue to function. Also, this does not protect a worker who is directly in the path of the laser beam. Laser radiation is especially damaging to the eyes of such workers.

Continued operation of the laser system is especially important in applications such as laser rangefinders, where the high-energy laser beam must pass through a protective rangefinder window. Dust or dirt on this window may absorb sufficient energy to cause localized overheating and destruction of the window. As in the case of personnel protective device, this window should be capable of protecting the rangefinder laser (here, against environmental damage, such as from rain or wind-blown dust) while permitting continued effective laser operation.

Protective devices using reflectors to reflect away incident infrared laser beams must be highly reflective in the infrared region, while permitting transmission of visible light. Unless a very high percentage of the incident infrared radiation is reflected, the portion absorbed by the protective device may be sufficient to cause localized overheating, thermal shock and permanent damage to the protective device.

Thus, there is a continued need for effective protective windows to protect personnel and equipment from damage from high-energy lasers while permitting continued operation of the overall system, at least temporarily.

It is, therefore, an object of this invention to provice a protective window for use with high-energy infrared lasers which overcomes the above-noted problems.

Another object of this invention is to provide an eye protection means for personnel subjected to high-energy laser radiation.

Still another object of this invention is to provide a self-cleaning window for use with high-energy lasers.

A further object of this invention is to improve the reflectance of high-reflectance protective surfaces.

Yet another object of this invention is to provide a means for protecting radiation sensors from high-energy infrared radiation.

SUMMARY OF THE INVENTION

The above objects, and others, are accomplished in accordance with this invention, basically, by providing a visible-light transmitting protective window having a dichroic coating which primarily reflects incident infrared radiation while primarily transmitting incident visible light and which has a further overcoating on at least one window surface of a material which rapidly vaporizes cleanly away without residue when subjected to intense infrared radiation. In a preferred embodiment, channels are formed within the window through which an absorbing fluid may be circulated to absorb the unwanted wavelengths that might pass through the front surfaces of the window and carry the heat to some remote location for safe cooling.

BRIEF DESCRIPTION OF THE DRAWING

A preferred embodiment of the protective window of this invention is illustrated in the drawing, wherein.

DETAILED DESCRIPTION OF THE INVENTION

Figure 1:
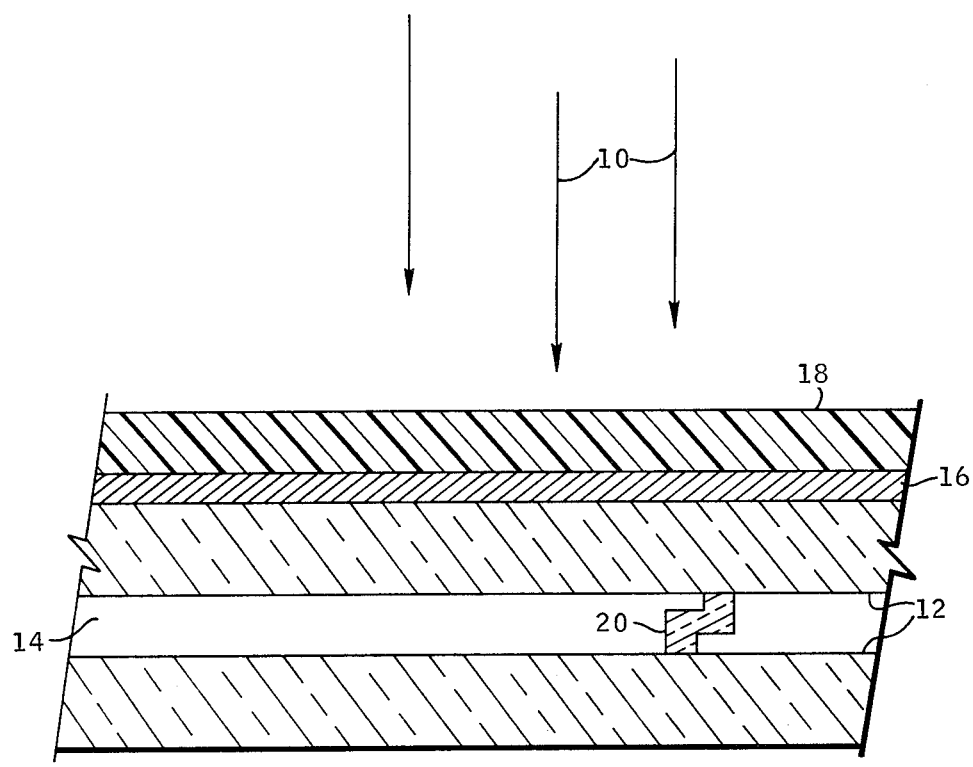
FIG. 1 shows a transverse section through a portion of the protective window.

A section through a preferred embodiment of a window suitable for protection against high-energy infrared radiation from a laser, nuclear flash or other intense source, coming from the general direction indicated by arrows 10 is shown in FIG. 1.

The window basically includes a visible-light transparent window structure 12 of glass, quartz, sapphire or the like. As seen in the illustrated embodiment, transparent window 12 may consist of two spaced sheets or plates with a channel 14 therebetween. A suitable infrared radiation absorbing fluid may be circulated through channel 14 to remove heat from window 12. Any suitable conventional pump and heat dissipating means (not shown) may be used. Channel 14 may have any suitable configuration. If desired, channel 14 may be in the form of tubes formed within a single plate window 12.

The transmission of thin sheets of fused silica glass is very high at infrared wavelengths. A 1 mm thick glass window 12 rejects about 7% of incident infrared radiation by surface reflection and absorbs about 13%, transmitting the balance. A water filled channel 14 having a thickness of about 2.5 cm absorbs effectively 100% of incident infrared radiation. Often, however, it is preferred to use some other infrared absorbing fluid which matches the index of refraction of the window and channel supports. Typically, an aqueous solution of 90% gylcerol by weight may be used, matching the index of refraction of fused silica.

The two windows 12 may be held in the desired spaced relationship by any suitable supports 20. Preferably, the supports are stepped or otherwise offset so that no radiation passes from one window 12 to the other without passing through the fluid.

An infrared radiation reflecting coating or layer 16 is provided on the surface of window 12 which is oriented toward the direction from which infrared radiation 10 is expected to come. Layer 16 is chosen to reflect most of the incident infrared radiation while transmitting most of the incident visible light.

Layer 16 is overcoated with coating 18 of a material which very rapidly vaporizes without leaving a residue when subjected to very intense infrared radiation. Without coating 18, dirt or dust on the surface of layer 16 will rapidly absorb heat when subjected to very intense infrared radiation. This localized high heat would be conducted to layer 16 and window 12 and would cause rapid destruction of these materials. However, when coating 18 rapidly vaporizes, any dirt or dust on the surface of coating 18 will be carried away with the rapidly vaporizing coating. Coating 18 vaporizes so rapidly that it appears almost to "explode" away.

The embodiment shown in FIG. 1 is especially suitable for use in protective devices in circumstances where very high energy infrared lasers are likely to accidentally or intentionally scan across the device. Typical of these applications would be goggles for use by experimenters or others using such lasers, windows looking into rooms in which such lasers are being used for experimental purposes, production welding or cutting, etc., canopies for aircraft which might encounter laser weapons, etc.

In some applications, the absorbing fluid channels 14 would not be required where the expected laser energy is not critically high. Also, in some circumstances, the reflecting layer 16 might be omitted and a vaporizable layer 18 might be desirably formed on both sides of window 12. Typical of these circumstances would be the case where window 12 is a protective cover in front of a laser signaling device or weapon which is activated only occasionally. In that case, dirt on either surface of window 12 could serve as a heat absorbing nucleatin center and cause destruction of the window when the laser is activated. For this application, window 12 would comprise an infrared transparent material, such as germanium, with a rapidly vaporizable layer 18 on each surface thereof. As described above, the rapid vaporization of layer 18, upon operation of the laser, from each surface of window 12 would carry away all surface dust and dirt.

Figure 2:
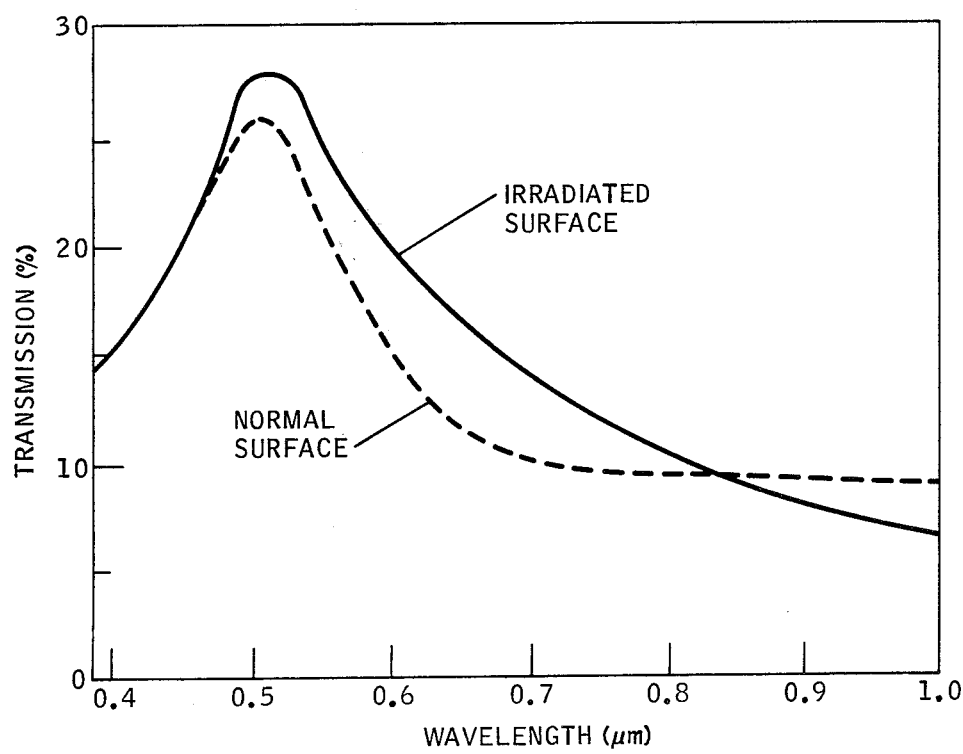
FIG. 2 is a chart showing transmission changes resulting from irradiating a reflecting layer in accordance with this invention.

FIG. 2 illustrates in graphical form the improvement in radiation transmission characteristics which results from treating a gold dichroic layer 16 with high energy infrared radiation by techniques described in detail below. As can be seen from FIG. 2, the visible light transmission characteristics (0.5 to 0.8μm) of the untreated or "normal" gold layer are improved by the irradiation treatment, while in the infrared radiation (0.8μm and beyond) region the treatment reduces transmission while increasing reflection. This makes a significant improvement in a protective window, increasing its usefulness for ordinary viewing, while improving its rejection of dangerous high-energy infrared radiation. The curves shown in FIG. 2 are plotted from experiments conducted as described in Example 1.

The window may comprise any suitable composition which is transparent to visible light primarily in the 0.4 to 0.7μm range. Typical materials include many glasses, quartz, and sapphire. Quartz or sapphire are preferred because of their excellent infrared transmission and ability to withstand thermal shocks.

Where the window may be subjected to rapid, intense heating but must remain useable, it is preferred that channels be provided within the window through which a heat absorbing fluid may be circulated. For best optical performance, the fluid should have substantially the same index of refraction as the window. The liquid should be pumped between the channels and a cooling means at a rate sufficient to carry off absorbed heat. While any suitable liquid may be used, water, aqueous solutions, or appropriate fluorocarbon liquids are preferred.

The dichroic coating which reflects away the high energy infrared radiation to prevent damage to objects beyond the window may have any suitable composition. Thin gold films are preferred, since they are easily formed and are highly effective. A preferred technique for applying the reflecting coating comprises vacuum depositing a gold layer onto the external window surface to thickness of from about 100 to 300 A, then exposing the gold layer to high energy infrared laser radiation for a brief period. In order to assure good adherence of the gold layer, it is often preferred that a 15 to 100 A layer of nickel be first applied to the window surface before formation of the gold layer. While any suitable infrared exposure may be used, in general it is preferred that the gold surface be exposed to infrared radiation in the 10.6 m region at power levels of from about 1500 to 2500 watt-sec/cm$^2$. Best results are obtained with a post-coating exposure of about 70 watts/cm$^2$ for about 30 seconds. This treatment produces a surprising improvement in infrared reflection efficiency coupled with a significant improvement in visible light transmission. While the reasons for these improvements are not fully understood, it is thought that they result from face heating of the deposited gold which apparently melts smaller particles into a smooth layer of larger particles. The concentrated radiation causes sufficient localized heating without overheating and degrading the mass of the window. It has been further found that both the adherence and apparent hardness of the coating were greatly enhanced by this irradiation.

After formation of the infrared reflecting layer, it is preferred that the reflector-coated surface (and, if desired, the opposite surface) be overcoated with a thin protective layer of a material which is transparent to visible light and which will rapidly vaporize without residue when exposed to very high energy infrared radiation. It has been found that without this protective layer, dirt or dust which has accumulated on the reflective surface will rapidly absorb heat and cause thermal damage to the reflecting layer and window structure. Where the window includes the protective overlayer, the overlayer vaporizes so rapidly that surface dirt is "blown" away. It is important that no vaporization residue be left, which could itself serve as a thermal damage nucleation center.

Any suitable material may be used in the vaporizable coating. Typical materials include fluorocarbon, epoxy, silicone and polysulfide resins. Fluorinated ethylene-propylene resins are preferred because of their excellent properties for the above-described purpose. This coating may be applied in any suitable manner. Typical techniques include laminating a stretched film over the window, or coating by means of vacuum evaporation. The stretched film appears to give the best optical properties. While the coating may have any suitable thickness, from about 0.001 to 0.005 inch is preferred.

The following examples describe preferred embodiments of methods for making the protective windows of this invention. All parts and percentages are by weight unless otherwise indicated.

EXAMPLE I

A sheet of silica glass, about 6 inches square and 0.3 inch thick, is coated with layers of nickel and gold by vacuum evaporation. The nickel layer has a thickness of about 100 A and the gold about 200 A. Reflectance of this surface is tested and found to be about 94.7 percent at a wavelength of 10.0 micrometers, about 94.4% at 10.5$\mu$m and about 94.8% at 11.0$\mu$m. Portions of the gold layer are then scanned with an 80-watt 10.6$\mu$m $CO_2$ laser focused to 3-mm diameter spot (1.1 kW/cm$^2$) so that each area is exposed for about 3 minutes. Transmission characteristics are measured with a Beckman DK-1 spectrometer before and after irradiation and the results are plotted in FIG. 2. As can be seen from these curves, transmission in the visible region (0.5 to 0.7$\mu$m) is increased, while transmission in the infrared region (above 0.8$\mu$m) is decreased. The gold layer is then overcoated by vacuum evaporation with a 0.001 inch layer of FEP-Teflon 856-200, a fluorinated ethylenepropylene polymer available from E. I. duPont de Nemours and Co. The coated glass sheet is then mounted in a frame with the uncoated surface spaced about 0.5 inch from a similar but uncoated glass sheet. The inter-sheet space is sealed around the edges of the assembly and fluid connections are provided on opposite sides of the frame so that fluids may be passed through the inter-sheet space. A 90% aqueous glycerol solution is then passed through the assembly at a rate proportional to the thermal absorption rate. The resulting protective window is tested by exposing the coated surface to a focused 10.6$\mu$m $CO_2$ laser beam at about 2.0 kW/cm$^2$. The Teflon coating is seen to "explode" clearly away within about 0.05 second after first exposure. No further changes are seen with further exposure. The underlying gold layer is seen to continue to reflect nearly all of the incident radiation, residual heat absorbed in the glass layer and radiant energy passing through the glass is carried away by the solution.

EXAMPLE II

A protective cover window for a high power infrared laser system is prepared by coating both sides of a 0.5 inch thick disk of potassium chloride with 0.05 inch layers of Teflon FEP-120, a fluorinated ethylene-propylene polymer available from E. I. duPont de Nemours, Inc. A second disk is provided without the coating. Each disk is exposed to an outdoor environment for about 10 days and accumulates a surface coating of dust, dirt, etc. Each disk is then placed in front of a 10.6$\mu$m $CO_2$ laser operating at about 2 megawatts. When the coated disk is exposed to the laser, the Teflon coating almost instantaneously evaporates, carrying away the surface dirt and leaving a clean, transparent window. The window continues to transmit the radiation without degradation. When the uncoated potassium chloride disk is exposed to the radiation it is severely damaged.

EXAMPLE III

A four inch disk of high silicate glass having a thickness of about 0.1 inch is coated with an 80 micron gold layer by vacuum evaporation over a nickel flash coat. The gold layer is then overcoated with a 0.002 inch layer of a silicone resin. The resulting protective window is substantially transparent to visible light while reflecting nearly all incident infrared radiation. The coated surface is then exposed to a 10.6 m laser operating at about 1 megawatt focused to cover about a 2-mm spot. The resin overcoating almost instantaneously vaporizes, carrying all surface contaminants with it. The clean gold layer thus exposed continues to reflect most of the incident radiation.

While certain preferred materials, structures and relationships are described in conjunction with the above description of preferred embodiments, these may be varied as described above, where suitable, with similar results.

Other ramifications, modification and applications of the present invention will become apparent to one skilled in the art upon reading this disclosure. These are intended to be included within the scope of the invention as defined in the appended claims.

I claim:

1. A protective cover window for use with high energy infrared lasers which comprises:
    a plate which is substantially transparent to infrared radiation, positioned in the path of radiation from an infrared laser, and
    a coating on at least one surface of said plate, said coating comprises a fluorinated ethylene-propylene polymer which rapidly vaporizes without leaving a residue when subjected to intense infrared radiation,
    whereby any surface contamination on said coating is carried away with the vaporizing material.

2. The protective window according to claim 1 wherein said coating has a thickness of from about 0.001 to about 0.005 inch.

3. A method of making a protective window for protection against high energy infrared laser radiation which comprises:
    providing a sheet which is substantially transparent to visible light,
    forming a layer of gold on one surface of said sheet to a thickness of from about 100 to 300 Angstroms,
    exposing said layer to infrared radiation at a power level of from about 1500 to about 2500 watt-sec/cm$^2$,
    forming a second layer over said gold layer of a material which is substantially transparent to visible light and which vaporizes without residue when subjected to intense infrared radiation.

4. The method according to claim 3 wherein said second layer comprises a fluorinated ethylene-propylene polymer and is formed to a thickness of from about 0.001 to 0.005 inch.

5. The method according to claim 3 further including the steps of forming channels within said sheet, said channels adapted to have an infrared radiation absorbing fluid flowed therethrough.

6. A method of making a protective window for a high energy infrared laser which comprises:
providing a sheet which is substantially transparent to infrared radiation, and
coating at least one surface of said sheet with a material comprising a fluorinated ethylene-propylene polymer which vaporizes without leaving a residue when subjected to intense infrared radiation,
whereby when a high energy laser beam is directed through said window said material vaporizes, carrying away any contamination on the surface thereof.

7. The method according to claim 6 wherein said material is coated to a thickness of from about 0.001 to 0.005 inch.

8. A method of protecting an object from radiation from a high energy infrared laser which comprises:
placing a sheet which is substantially transparent to visible light between an object and a high energy infrared laser;
forming a thin layer of gold on the laser side of said sheet, said gold layer capable of transmitting a substantial portion of incident visible light while substantially entirely reflecting incident infrared radiation;
coating said gold layer with a material which vaporizes without leaving a residue when subjected to said laser radiation;
exposing such coating to weather for a period likely to cause dirt and other contamination to be deposited thereon; and
exposing said layer to said laser radiation, whereby said material rapidly vaporizes, carrying away the contamination and preventing thermal damage to said sheet while leaving said gold coated sheet transparent to visible light and reflecting to infrared radiation.

9. The method according to claim 8 wherein said coating is formed by coating said gold layer with a fluorinated ethylene-propylene polymer to a thickness of from about 0.001 to 0.005 inch.

10. The method according to claim 8 wherein said sheet comprises fused silica glass and including the further step of circulating a solution consisting essentially of about 10 weight percent water and about 90 weight percent glycerol through channels within said sheet.

* * * * *